United States Patent [19]

Story

[11] Patent Number: 5,738,871
[45] Date of Patent: Apr. 14, 1998

[54] PHARMACEUTICAL FORMULATIONS

[75] Inventor: Michael John Story, Glenside, Australia

[73] Assignee: Cortecs Limited, Middlesex, United Kingdom

[21] Appl. No.: 430,500

[22] Filed: Apr. 28, 1995

Related U.S. Application Data

[62] Division of Ser. No. 242,078, May 13, 1994, Pat. No. 5,532,002.

[51] Int. Cl.$^6$ ........................... A61K 9/48
[52] U.S. Cl. ........................ 424/451; 424/456; 424/489; 424/463
[58] Field of Search ................... 424/451, 452.18, 424/489, 463

[56] References Cited

U.S. PATENT DOCUMENTS

| | | | |
|---|---|---|---|
| 4,572,915 | 2/1986 | Crooks | 514/458 |
| 4,795,642 | 1/1989 | Cohen | 424/456 |
| 4,816,259 | 3/1989 | Matthews et al. | 424/463 |
| 4,944,949 | 7/1990 | Story | 424/456 |
| 5,188,688 | 2/1993 | Boardman et al. | 156/69 |
| 5,455,045 | 10/1995 | Samuels et al. | 424/451 |

FOREIGN PATENT DOCUMENTS

| | | |
|---|---|---|
| 107085 | 5/1984 | European Pat. Off. . |
| 127297 | 12/1984 | European Pat. Off. . |
| 196085 | 10/1986 | European Pat. Off. . |
| 292050 | 11/1988 | European Pat. Off. . |
| 56-65820 | 6/1981 | Japan . |
| 1233218 | 9/1989 | Japan . |

OTHER PUBLICATIONS

English language abstract of JP 56–065820.

English language abstract of JP 1,233,218.

*Primary Examiner*—Thurman K. Page
*Assistant Examiner*—William E. Benston, Jr.
*Attorney, Agent, or Firm*—Hale and Dorr LLP

[57] ABSTRACT

Hard gelatin capsules contain: (a) a fat-soluble nutrient, such as a fat-soluble vitamin (A, D, E or K) or an unsaturated fatty acid glyceride; (b) a nonionic surfactant, such as a polyoxyethylated (optionally hydrogenated) castor oil, and/or a polyethylene glycol; (c) a gelatin softening agent such as glycerol, propylene glycol or, preferably, glyceryl monooleate; and optionally (d) water. The problems of embrittlement conventionally encountered with hard gelatin capsules containing fat-soluble nutrients are reduced or avoided.

22 Claims, No Drawings

PHARMACEUTICAL FORMULATIONS

This application is a division, of application Ser. No. 08/242,078, filed May 13, 1994 now U.S. Pat. No. 5,532,002.

This invention relates to the formulation of fat-soluble nutrients.

Fat-soluble nutrients include mono-, di- or tri-glycerides having at least one mono- or poly-unsaturated fatty acid chain, as well as the fat-soluble vitamins A, D, E and K. Certain of the fat-soluble glyceride nutrients are often referred to as essential fatty acids (EFAs), although more properly they should perhaps be called glycerides of essential fatty acids.

Fat-soluble nutrients including glycerides and vitamins are susceptible to malabsorption. In the extreme, there are conditions associated with malabsorption, particularly of EFAs, such as cystic fibrosis, chronic pancreatitis, biliary atresia, muscular dystrophy, multiple sclerosis and food allergies. These conditions have been linked with deficiencies of one or more of the fat-soluble nutrients.

As for the vitamins, vitamin A is necessary for growth and differentiation of epithelial tissue and is required for growth of bone, reproduction and embryonic development. It has an essential role to play in the function of the retina: vitamin A deficiency interferes with vision in dim light, a condition known as night blindness.

Vitamin D deficiency results in rickets. The vitamin D group of compounds regulates calcium absorption by the small intestine and calcium metabolism in bone.

It is not entirely clear what is the effect of deficiency of vitamin E. However, this vitamin may be important for its properties as a potent anti-oxidant. Furthermore, it appears to be important in maintaining the integrity and stability of biological membranes as well as being important in controlling prostaglandin synthesis.

Vitamin K is a dietary substance which is essential for the normal biosynthesis of several factors required for clotting of blood.

From the above, it is clear that it is essential that the individual both ingest and absorb adequate quantities of fat-soluble nutrients, be they essential fatty acid glycerides or fat-soluble vitamins. The absorption of fat-soluble nutrients is dependent on the individual's capacity to digest and absorb fat, which is generally achieved physiologically through the lymphatic system. This is well established for fatty acid glycerides, and it has been demonstrated in humans that the lymphatic pathway is the major absorption pathway for vitamin E.

Adequate pancreatic enzyme, bicarbonate and bile output are required for lymphatic absorption. If the diet is too low in fat, there may be inadequate secretion of emulsifying substances which may lead to poor fat-soluble nutrient absorption. Conversely, if the diet is excessively high in fat such that the gall-bladder and pancreatic system are overloaded and unable to process all the fat, then absorption may be reduced. It may be that the lymphatic system, or the earlier stages in the fat-absorption process that lead to the lymphatic system, of those individuals who have a deficiency in one or more fat-soluble nutrients is defective in some way and so prevents proper absorption. If this is correct, it explains why the conventional administration of excess additional quantities of the nutrient in question will not solve the problem.

Even in those individuals without impaired lymphatic fat absorption capabilities, the efficiency of absorption of, for example, vitamin E is relatively poor, being about 20 to 40%, and so there is a general need to be able to improve absorption of fat-soluble nutrients.

The body does have an alternative absorption route through the portal system. This pathway applies to water-soluble substances and to poorly water-soluble substances which have been solubilised, for example by non-ionic surfactants. It has been demonstrated that vitamin E is better absorbed from orally administered aqueous solutions than from oily solutions, and that vitamin E in aqueous solution is absorbed by patients suffering from fat-malabsorption diseases.

Capitalising on this alternative portal route, aqueous solutions containing micellised vitamin preparations have been available for many years. U.S. Pat. No. 4572915, for example, relates to clear micellised solutions of fat-soluble essential nutrients. Unfortunately, aqueous micellised preparations can have a number of drawbacks, such as stability, taste, smell and inconvenience, all of which are factors which make patient compliance difficult.

GB-A-2145331 discloses various surfactant-containing compositions of vitamins A and E in soft elastic gelatin capsules. The surfactant used is polysorbate 80, which is a common name for a polyoxyethylene sorbitan ester surfactant. Certain of the formulations exemplified lead to the production of unstable emulsions, when they are mixed with water.

Although capsules are a highly suitable means of administration of fat-soluble nutrients, it would be preferable to use hard gelatin capsules rather than soft gelatin capsules. This is because hard gelatin capsules have more consumer appeal, and because there is a more open supply market for hard gelatin capsules. However, there is a problem: liquid formulations of a fat-soluble nutrient and a nonionic surfactant tend to cause embrittlement of hard gelatin capsules, and so lead to unacceptably poor stability characteristics of hard gelatin capsules filled with such formulations. It is to providing a solution to this problem that the present invention is addressed.

It has been found that a gelatin softening agent, such as may conventionally be used in the manufacture of soft gelatin capsules, can, if incorporated into the capsule contents, significantly reduce embrittlement. Possibly this is because the softening agent can leach into the gelatin shell at a sufficient rate and in a sufficient amount to prevent embrittlement, but this is only a suggestion for the basis of the observed efficacy.

According to a first aspect of the invention, there is provided a hard gelatin capsule containing: (a) a fat-soluble nutrient; (b) a nonionic surfactant; (c) a gelatin softening agent; and optionally (d) water.

Hard gelatin capsules, sometimes also known as hard-shell gelatin capsules, are well known. The shells are generally supplied to the pharmaceutical formulator in two interlocking U-sectioned shell portions, one of which is filled with the capsule contents and the other of which is placed over the filled shell portion to act as a cap. The two shell portions can then be sealed by any convenient means such as by gelatin banding, which is preferred, or by the LICAPS system marketed by the Capsugel division of Parke Davis. (The word LICAPS is a trade mark.) Hard gelatin capsule shells are available from the Elanco division of Eli Lilly, from the Capsugel division of Parke Davis and from many other sources. They come in a variety of standard sizes, for example sizes "00", "0", "1", "2" and "3".

The term "fat-soluble nutrient" includes the fat-soluble vitamins and glycerides of fatty acids, that is to say mono-, di- or tri-glycerides optionally having at least one mono- or poly-unsaturated fatty acid (which may be an essential fatty acid) chain. Essential fatty acid glycerides include glycerides of essential fatty acids, which may for example be from $C_{14}$ to $C_{22}$ with, for example, from 1 to 7, for example 2 to 5, unsaturated bonds. There are two principal EFA series, the omega-3 and omega-6 series; the number denotes the number of the first double bond from the methyl end of the hydrocarbon chain of the fatty acid residue in the glyceride. Linoleic acid is an omega-6 EFA and alpha-linolenic acid is an omega-3 EFA. The glycerides of oleic acid, which is a mono-unsaturated fatty acid, are other important fat-soluble nutrients.

The omega-6 essential fatty acids are more prevalent in plant than animal food sources in western diets. Linoleic acid is found abundantly in many warm weather vegetable seed oils, for example safflower, corn, soya bean and sunflower oil. Gamma-linolenic acid is found in evening primrose oil (EPO), borage oil and oil of blackcurrant. The omega-3 EFAs are found predominantly in fish oils and to a smaller extent in cold weather seed oils such as flaxseed and linseed. The principal omega-3 EFAs are eicosapentaenoic acid (EPA) and docosahexaenoic acid (DHA). Vegetable oils may also include glycerides of saturated fatty acids including palmitic acid and stearic acid.

Other esters of fatty acids are also within the term "fat-soluble nutrient". Examples include esters with lower (eg $C_1$-$C_6$) alcohols, such as ethyl esters.

More than one fat-soluble nutrient may be present. Natural oils which are a mixture of fat.-soluble nutrients may be used in capsules in accordance with the present invention. Example of suitable natural oils which can serve as fat-soluble nutrients include sweet almond oil, arachis oil, corn oil, cottonseed oil, grape seed oil, olive oil, safflower oil, hybrid safflower oil (high oleic acid), sesame oil, soyabean oil, sunflower oil and high oleic sunflower oil. Table 1 shows typical compositions of the acids which are presented as glycerides in various natural oils.

TABLE 1

|  | C16:0 | C18:0 | C18:1 | C18:2 | C18:3 |
|---|---|---|---|---|---|
| Sweet Almond Oil | 6 | 2 | 70 | 22 |  |
| Arachis Oil | 8 | 3 | 56 | 26 |  |
| Corn Oil | 7 | 3 | 43 | 39 |  |
| Cottonseed Oil | 19 | 2 | 33 | 39 |  |
| Grape Seed Oil | 2 max | 7 max | 10–25 | 62–76 max | 2 |
| Olive Oil | 10 | 2 | 81 | 5 | 1 |
| Safflower Oil | 6 | 2 | 12 | 78 | 1 |
| Hybrid Safflower Oil (high Oleic Acid) | 5 |  | 81 | 12 |  |
| Sesame Oil | 9 | 4 | 45 | 40 |  |
| Soybean Oil | 9–16 | 1–2 | 19–26 | 50–57 | 6–9 |
| Sunflower Oil | 5–11 | 4–7 | 14–30 | 55–74 | 1 max |
| High Oleic Sunflower Oil | 4 | 4 | 80 | 9 |  |

Natural oils containing essential fatty acids of the omega-6 family include evening primrose oil, borage oil and blackcurrant seed oil. The percentage composition of the principal fatty acids in these oils is shown in Table 2.

TABLE 2

|  | C16:0 | C18:0 | C18:1 | C18:2 | C18:3 | C18:4 |
|---|---|---|---|---|---|---|
| Evening Primrose Oil | 6 | 2 | 10 | 72 | 10 | — |

TABLE 2-continued

|  | C16:0 | C18:0 | C18:1 | C18:2 | C18:3 | C18:4 |
|---|---|---|---|---|---|---|
| Borage Oil |  |  |  | 37 | 24 | — |
| Blackcurrant Seed Oil | 6 | 1 | 11 | 44 | 33 | 4 |

Blackcurrant seed oil is of additional interest in that the C18:3 is made up of alpha-linolenic acid (for example, about 15%) as well as the gamma-linolenic acid (for example about 18%). The latter is the principal component of the C18:3 of evening primrose oil and borage oil.

Oils containing EFAs of the omega-3 family include fish oils, which can be refined to contain various levels of eicosapentaenoic acid (EPA) and docosahexaenoic acid (DHA). Examples would be:

Average —12% EPA and 8% DHA

Intermediate —20% EPA and 10% DHA, or

High —25% EPA and 12% DHA

Sardine oil and salmon oil are examples of fish oils having high levels of EPA and DHA.

Linseed oil is a source of alpha-linolenic acid.

Fat-soluble vitamins include vitamins A, D, E and K.

The term "vitamin A" as used in this specification not only includes retinol and its active esters, but also other compounds that exhibit the biological properties of retinol. Carotene, or provitamin A, is a very potent source of retinol and is therefore regarded as being within the definition of "vitamin A" for the purpose of this specification.

The two principal D vitamins are vitamin $D_2$ (calciferol) and vitamin $D_3$ (cholecalciferol). There appears to be no practical difference between the two. The term "vitamin D" as used in this specification includes all active forms.

The term "vitamin E" as used in this specification includes the group of chemically related compounds of which the most active is alpha-tocopherol. Naturally occurring vitamin E has the d-configuration, as opposed to a mixture of synthetic alpha-tocopherol which is designated as dl-alpha-tocopherol. d-alpha-tocopherol can suffer from instability in some instances and it can then be replaced by the more stable d-alpha-tocopheryl acetate form. All compounds and derivatives having the biological activity of d-alpha-tocopherol are included within the term "vitamin E".

Natural vitamin E is available as a by-product of vegetable oil production, where it is extracted as the alcohol d-alpha-tocopherol, or as the synthesised acetate which is generally more stable than the alcohol. The natural (d-) forms are more active than the synthesised (dl-) form. Relative activities are:

| dl-alpha-tocopheryl acetate | 1000 iu/g |
| dl-alpha-tocopherol | 1100 iu/g |
| d-alpha-tocopheryl acetate | 1360 iu/g |
| d-alpha-tocopherol | 1490 iu/g | d-alpha-tocopherol is not normally available as a highly purified oil (generally up to 67% purity), whereas the others are generally available in greater purity in their common commercially available forms; for example, certain commercially available d-alpha-tocopheryl acetate is available at 81% purity, and this is quite acceptable in practice.

Vitamin K is a dietary substance which is essential for the normal biosynthesis of several factors required for clotting of blood. Vitamin K activity is associated with two natural substances, vitamin $K_1$ (phytonadione) and vitamin $K_2$ (methaquinone). Again, the term "vitamin K" as used in this specification covers all compounds having vitamin K activity.

The amount of fat-soluble nutrient present will depend upon its nature. For glycerides and mixtures of them and vitamin E, amounts of from 50 to 300 mg per capsule are preferred, with from 150 to 250 mg being typical. For vitamin A, amounts of from 5 to 150 mg per capsule are suitable, with from 10 to 50 mg being typical. For vitamin K, amounts of from 0.1 to 10 mg per capsule, typically 0.5 to 5 mg, may be present. For vitamin D, much smaller amounts, such as from 0.001 to 0.1 mg, typically 0.005 to 0.05 mg, may be present. Clearly, the amount present will also depend upon the size of capsule used. So, for example, up to 300 i.u. of vitamin E could be formulated in a single capsule by means of the present invention.

Component (b) of a capsule in accordance with the first aspect of the invention comprises a nonionic surfactant.

Preferred nonionic surfactants are polyoxyethylated compounds. The degree of polyoxyethylation may range from about 15 to about 60. A polyoxyethylation range of from 20 or 30 to 45 is preferred. Surfactants preferred for use in this invention include polyoxyethylated castor oils and polyoxyethylated hydrogenated castor oils. POE(40) hydrogenated castor oil is particularly suitable. Commercially available samples are sold under the trade mark CREMOPHOR RH40 (from BASF) or CRODURET 40 from Croda. A suitable polyoxyethylated castor oil is POE(35) castor oil, which is available commercially under the trade name CREMOPHOR EL (from BASF) or ETOCAS 35 (from Croda). It has generally been found that an unhydrogenated castor oil-derived surfactant is preferable for use when formulating vitamin E whereas a unhydrogenated castor oil, or a mixture of hydrogenated and unhydrogenated castor oils, is preferable when preparing capsules containing glycerides of essential fatty acids and vitamins A, D and K. It will be appreciated that the surfactant, like the fat-soluble nutrient, may be present either as a single entity or as a mixture.

Polyoxyethylated (optionally hydrogenated) castor oils are not the only surfactants which can be used in this invention. Other suitable polyoxyethylated surfactants include polyoxyethylated glycol monoethers, polyoxyethylated fatty acids and polyoxyethylated sorbitan fatty esters or polysorbates, such as those sold under the trade mark TWEEN for example TWEEN 20 or TWEEN 80). Other nonionic surfactants are also useful, including sorbitan fatty acid esters, polyoxamers, polyethylene glycol fatty acid esters and polyethoxylated glyceryl fatty acid esters and other polyethoxylated polyalcohol fatty acid esters.

Examples of such surfactants are the surfactants sold under the trade mark GELUCIRE and LABRAFIL by Gattefosse; these surfactants are the products of the alcoholysis reaction between triglyceride components of vegetable oils or fats and hydroxyl groups of polyalcohols. The lipophiles are saturated natural fats or oils and are essentially hydrogenated palm kernel and palm oil. The hydrophiles are polyoxyethyleneglycol polyalcohols with molecular weights between 300 and 1500.

Certain surfactant/oil combinations tend to give better results than others, as might be expected when working with a complex mixture of heterogeneous species. Nevertheless, it is quite within the capability of those skilled in the art to prepare adequate and even excellent formulations when working within the teaching of this specification and using no more than routine experimentation.

Nonionic surfactants preferred for use in this invention have a hydrophile-lipophile balance (HLB) value of at least 10. For example, POE (20) sorbitan tristearate, sold under the trade mark TWEEN 65, is suitable and has an HLB value of 10.5. In many instances, however, an HLB value of at least 12 will be preferred: POE (35) castor oil has an HLB value of 12.5 and POE (40) hydrogenated castor oil has an HLB of 13.0.

Whatever the precise chemical structure of the surfactant or surfactants used, it is generally preferred to use one or more of those that have been already cleared for human ingestion. Therefore, surfactants with a low toxicity are preferred. For example, surfactants having an LD50 exceeding 10 g/kg and preferably 15 g/kg, are generally suitable. The absence of other side effects is of course also appropriate. Although surfactants which have already been approved for human ingestion are naturally preferred, the use of other surfactants is not ruled out, not least because they may in time come to be approved for human ingestion.

The surfactant can be present in any suitable amount, for example from 30% (w/w) to 99% (w/w), based on the total weight of the formulation used for filling the capsules. For example, surfactant levels may range from 50 to 500 mg per capsule, with 200–460 mg being typical in some cases, although the amounts may be lower or even higher. In cases of small quantities of active (eg vitamins A, D, K) it is not actually necessary to have so much surfactant, but it is left in for convenience in filling and so as to not have so much dead space in the capsule. It is difficult to fill capsules smaller than size "2" hard gelatin capsules, but small capsules may sometimes be appropriate.

The ratio of surfactant:fat-soluble nutrient will generally be at least 1:1. A ratio of from 1:1 or 1.25:1 to 1.75:1 or 2:1 will be typical, and ratios of from 1.0:1 to 1.5:1 will often be used in practice. The ratios applied to vitamins A, D and K tend to be very high for surfactant:active (10:1, 33000:1, and 330:1 respectively), but these high ratios are not in fact anywhere near necessary.

Component (c) is a gelatin softening agent. The gelatin softening agent can be any compatible material that functions appropriately. Generally, suitable materials can be found by reference to the art of manufacturing soft gelatin capsules, where such materials are incorporated into the mix that goes to form the gelatin wall itself. Particularly suitable gelatin softening agents are glycerol, propylene glycol and glyceryl mono-oleate. Sorbitol may also be suitable.

Glyceryl mono-oleate has a further advantage in that it can enhance the stability of the mixture used to fill the hard gelatin capsules. This can be useful if the particular combination of ingredients used would otherwise have a tendency to result in phase separation. For example, a mixture of CREMOPHOR RH40 POE (40) hydrogenated castor oil and various oils (such as evening primrose oil, fish oil, borage oil or blackcurrant seed oil) may under certain conditions separate into two phase; this can be counteracted by the addition of glyceryl mono-oleate.

Although any of the gelatin softening agents (particularly those preferred agents discussed above) may be found to be highly effective when used individually, there appears to be a further benefit to be had when glyceryl mono-oleate is used in conjunction with another gelatin softening agent, such as glycerol or propylene glycol. This further benefit is an enhancement of the gelatin softening action.

The amount of gelatin softening agent used will generally be selected adequately to prevent embrittlement of the capsule, but insufficient to cause ready deformability of the capsule. Regard should be had to the fact that hard gelatin capsules are often sold in blister packs, and so the capsule shells should be tough enough to withstand being pushed out of such packs without unacceptable deformation. In general terms the gelatin softening agent should for preference be present in an amount up to 10% (w/w) based on the weight of the non-oil components, for example from 3% to 6%, unless the agent comprises glyceryl mono-oleate, in which case the glyceryl mono-oleate can be present in an amount up to 30% (w/w), on the same basis, for example from 3% or 5% to 20% or 25%.

Water may be present in formulations in accordance with the invention. Its presence is not necessarily obligatory, but in some instances added or inherent water may be found to be advantageous. For example, mixtures of particular proportions of certain surfactants and gelatin softening agents (such as a mixture of CREMOPHOR RH40 POE (40 ) hydrogenated castor oil and 4% glycerol) are virtually opaque at room temperature and may paradoxically be clarified by the addition of water. Water may be added up to an amount of 5 or 6% (w/w) based on the weight of the non oil components, for example from 2 to 4%. Even if it is not specifically added, water may be provided when the surfactant is added as certain surfactants are hygroscopic.

The fat-soluble nutrient(s), the surfactant(s) or PEG(s), the gelatin softening agent and optionally the water may be the only ingredients in the capsule contents. It is not necessary for any further ingredient to be present, but under some circumstances additional materials may be present. One particular extra ingredient that may be suitable in some circumstances is an antioxidant; the precise type of antioxidant will depend upon the type of oil being used. It is also possible, but not necessary, to incorporate extra excipients if desired.

Generally liquid formulations comprising the contents of hard gelatin capsules in accordance with the first aspect of the invention themselves form a second aspect of the invention.

Therefore, according to a second aspect of the invention, there is provided a formulation comprising (a) a fat-soluble nutrient; (b) a nonionic surfactant; (c) a gelatin softening agent; and optionally (d) water.

According to a third aspect of the invention, hard gelatin capsules in accordance with the first aspect of the invention described above can simply be prepared by at least partially filling hard gelatin capsule shells with a formulation of the second aspect. If desired, the components may be heated (say to about 60° C.) and then cooled (say to 40° C.) before encapsulation. Conventional filling and, if required, sealing techniques may be used, although the use of such techniques which are themselves innovative is not of course precluded.

According to a fifth aspect of the invention, there is provided a process for preparing a formulation in accordance with the second aspect, the process comprising admixing the ingredients together.

Preferred features of the second to fifth aspects of the invention are as for the first aspect, mutatis mutandis.

The invention will now be illustrated by the following examples.

EXAMPLE 1

Capsules of 200 mg Evening Primrose Oil per capsule were prepared using the following proportions, in size "O" hard gelatin capsules:

|  | mg per capsule |
| --- | --- |
| Evening Primrose Oil | 200 |
| POE (40) hydrogenated castor oil (CREMOPHOR RH40) | 360 |
| Glyceryl Mono-oleate | 40 |
| TOTAL | 600 |

The three ingredients were heated together with stirring, with the temperature being kept below 60° C. After cooling to below 40° C., the mixture was filled into capsules. These temperatures are indicative, but not restrictive. On storage at 25° C., the capsules were very strong and pliable after 3 months, and the mix was clear and of one phase.

EXAMPLE 2

Capsules of 200 mg Evening Primrose Oil per capsule were prepared using the following proportions, in size "O" hard gelatin capsules:

|  | mg per capsule |
| --- | --- |
| Evening Primrose Oil | 200 |
| POE (40) hydrogenated castor oil (CREMOPHOR RH40) | 210 |
| POE (35) castor oil (CREMOPHOR EL) | 90 |
| Glyceryl mono-oleate | 70 |
| Glycerol | 15 |
| Water | 15 |
| TOTAL | 600 |

The six ingredients were heated together with stirring, with the temperature being kept below 60° C. After cooling to below 40° C., the mixture was filled into capsules. These temperatures are indicative, but not restrictive. On storage at 25° C., the capsules remained strong and very pliable, with the mix being clear.

EXAMPLE 3

Capsules of 250 mg Evening Primrose Oil per capsule were prepared using the following proportions, in size "O" hard gelatin capsules:

|  | mg per capsule |
| --- | --- |
| Evening Primrose Oil | 250 |
| POE (40) hydrogenated castor oil (CREMOPHOR RH40) | 115 |
| POE (35) castor oil (CREMOPHOR EL) | 115 |
| Glyceryl mono-oleate | 90 |
| Glycerol | 15 |
| Water | 15 |
| TOTAL | 600 |

The six ingredients were heated together with stirring, with the temperature being kept below 60° C. After cooling to below 40° C., the mixture was filled into capsules. These temperatures are indicative, but not restrictive. On storage at 25° C., the capsules remained strong and very pliable, with the mix being clear.

EXAMPLE 4

Capsules of 250 mg fish oil (EPAMARINE—30% EPA +DHA) were prepared in the same manner as Example 3, except that 250 mg of fish oil was used per capsule in place of th 250 mg of Evening Primrose Oil used in Example 3. The capsules were also very strong and very pliable on storage at 25° C., and the mix remained clear.

EXAMPLES 5A TO 5Q

In order to exemplify the use of POE (40) hydrogenated castor oil (CREMOPHOR RH40) and POE (35) castor oil (CREMOPHOR EL) as solubilising agents for formulations for hard gelatin capsules, a number of natural oils were tested using either of the two surfactants alone with glyceryl mono-oleate, or as 50/50 mixtures of the two surfactants with glyceryl mono-oleate. The basic composition tested was:

|  | mg |
|---|---|
| Oil | 250 |
| Surfactant | 200 |
| Glyceryl mono-oleate | 120 |
| Water | 15 |
| TOTAL | 585 |

The results were as per the following table, with the coding:

*=clear mixture, satisfactory solubilisation of the oil in water
H=hazy mixture
2L=separation into 2 layers
PS=poor solubilisation of the oil in water
NT=not tested

|  | CREMOPHOR TYPE | | |
|---|---|---|---|
|  | RH40 | RH40/EL (50:50) | EL |
| A. Sweet Almond Oil | * | * | * |
| B. Arachis Oil | * | * | H; 2L; PS |
| C. Borage Oil | NT | * | NT |
| D. Blackcurrant Seed Oil | NT | * | NT |
| E. Cod Liver Oil | * | * | H; 2L; PS |
| F. Corn Oil | * | * | * |
| G. Cottonseed Oil | H | H | * |
| H. Fish Oil (30% EPA + DHA) | * | * | * |
| I. Grapeseed Oil | * | * | * |
| J. Halibut Oil | * | * | H; 2L |
| K. Linseed Oil | * | * | * |
| L. Olive Oil | * | * | H; 2L |
| M. Safflower Oil | * | * | H; 2L; PS |
| N. Hybrid Safflower Oil (high oleic acid) | * | * | H; 2L; PS |
| O. Sesame Oil | * | * | H; 2L; PS |
| P. Soyabean Oil | H | * | * |
| Q. Sunflower Oil | H | H | * |

The components were mixed together at temperatures between 40 and 50° C.

From the above, it is clear that each oil can be subjected to simple testing to determine the most suitable surfactant, or combination of surfactants. Glyceryl mono-oleate is very beneficial in enhancing solubilisation. If necessary, small amounts of glycerol can be added to any of the above formulations to improve pliability if required. The use of glyceryl mono-oleate at the level of this example is for illustrative purposes only. It may be used at different levels depending on the ease or difficulty in achieving a suitable mix in terms of clarity and solubilising capability.

EXAMPLE 6

Capsule mixes of 200 iu Vitamin-E per capsule were prepared using the following proportions, for size "1" hard gelatin capsules, the components being mixed together at a temperature between 40° and 50° C.:

|  | mg per capsule |
|---|---|
| d-alpha-tocopheryl acetate (1100 iu/g) | 200 |
| POE (35) castor oil (CREMOPHOR EL) | 205 |
| Glyceryl mono-oleate | 20 |
| TOTAL | 425 |

The temperature of mixing was approximately 50° C. The capsules were filled into hard gelatin capsules and sealed using the Licaps technique. The capsules were very strong and the contents were clear after storage for three months.

EXAMPLES 7-12

Capsule mixes of 200iu vitamin E per capsule were prepared using the following proportions for size "1" hard gelatin capsules, the fill weight being 425 mg per capsule and the components being mixed at 40°-50° C.:

| Example No |  | mg per capsule |
|---|---|---|
| 7 | d-alpha-tocopheryl acetate (1360 iu/g) | 147 |
|  | POE (35) castor oil (CREMOPHOR EL) | 258 |
|  | Glycerol | 10 |
|  | Water | 10 |
|  | TOTAL | 425 |
| 8 | d-alpha-tocopheryl acetate (1360 iu/g) | 147 |
|  | POE (35) castor oil (CREMOPHOR EL) | 248 |
|  | Glyceryl mono-oleate | 20 |
|  | Water | 10 |
|  | TOTAL | 425 |
| 9 | d-alpha-tocopheryl acetate (1100 iu/g) | 182 |
|  | POE (35) castor oil (CREMOPHOR EL) | 223 |
|  | Glycerol | 10 |
|  | Water | 10 |
|  | TOTAL | 425 |
| 10 | d-alpha-tocopheryl acetate (1100 iu/g) | 182 |
|  | POE (35) castor oil (CREMOPHOR EL) | 213 |
|  | Glyceryl mono-oleate | 20 |
|  | Water | 10 |
|  | TOTAL | 425 |
| 11 | dl-alpha-tocopheryl acetate (1000 iu/g) | 200 |
|  | POE (35) castor oil (CREMOPHOR EL) | 205 |
|  | Glycerol | 10 |
|  | Water | 10 |
|  | TOTAL | 425 |
| 12 | dl-alpha-tocopheryl acetate (1000 iu/g) | 200 |
|  | POE (35) castor oil (CREMOPHOR EL) | 195 |
|  | Glyceryl mono-oleate | 20 |
|  | Water | 10 |
|  | TOTAL | 425 |

EXAMPLE 13

Capsules of 50,000 iu vitamin A per capsule were prepared using the following proportions in size "2" hard gelatin capsules:

|  | mg per capsule |
| --- | --- |
| Vitamin A palmitate (1.7 m.i.u./g) | 30 |
| POE (40) hydrogenated castor oil (CREMOPHOR RH40) | 275 |
| Glycerol | 12.5 |
| Water | 12.5 |
| TOTAL | 315 |

The mixing of the components was at 40–50° C. Alternatively, POE (35) castor oil (CREMOPHOR EL) can be used as the surfactant.

EXAMPLE 14

Capsules of 400iu vitamin D per capsule, i.e. 10 microgram cholecalciferol per capsules, were prepared using the following proportions in size "2" hard gelatin capsules:

|  | mg per capsule |
| --- | --- |
| Vitamin D (Cholecalciferol) | 0.01 |
| POE (40) hydrogenated castor oil (CREMOPHOR RH40) | 290 |
| Glycerol | 12.5 |
| Water | 12.5 |
| TOTAL | 315.01 |

The mixing of components was at 40–50° C. Alternatively, POE (35) castor oil (CREMOPHOR EL) can be used as the surfactant.

EXAMPLE 15

Capsules of 1 mg vitamin K per capsule, present as vitamin K, or phytomenadione, were prepared using the following proportions in size "2" hard gelatin capsules:

|  | mg per capsule |
| --- | --- |
| Vitamin K | 1 |
| POE (40) hydrogenated castor oil (CREMOPHOR RH40) | 290 |
| Glycerol | 12 |
| Water | 12 |
| TOTAL | 315 |

The mixing of components was at 40–50° C. Alternatively, POE (35) castor oil (CREMOPHOR EL) can be used as the surfactant.

Note that combinations of vitamins E, A, and/or D can be achieved through sensible combinations of the formulations from the above examples.

EXAMPLE 16

A batch of capsules containing 100iu vitamin E per capsule was prepared, for size "1" hard gelatin capsules, using the following formulation:

|  |  | mg per capsule |
| --- | --- | --- |
| d-alpha-tocopherol (1000 iu/g) | 460 g | 100 |
| POE (35) castor oil (CREMOPHOR EL) | 1448 g | 315 |
| Glycerol | 46 g | 10 |
| Purified water | 46 g | 10 |

The mix was prepared by mixing and heating to approximately 50° C. The mix was encapsulated in size "1" LICAPS hard gelatin capsules with gelatin banding. After three months, the formulation was found to be stable in terms of vitamin E activity, and the capsules were very strong with adequate pliability after this storage time.

EXAMPLE 17

A batch of capsules containing 100 iu vitamin E and 10 mg beta-carotene per capsule was prepared, for size "1" hard gelatin capsules, using the following formulation:

|  |  | mg per capsule |
| --- | --- | --- |
| d-alpha-tocopherol (1000 iu/g) | 460 g | 100.1 |
| Beta-carotene (30% fluid suspension in Arachis Oil) | 154 g | 33.5 |
| POE (35) castor oil (CREMOPHOR EL) | 1294 g | 281.4 |
| Glycerol | 46 g | 10.0 |
| Purified water | 46 g | 10.0 |

The mix was prepared by mixing and heating to approximately 50° C. The mix was encapsulated in size "1" LICAPS hard gelatin capsules with gelatin banding. After three months the formulation was found to be stable in terms of vitamin E and beta-carotene activity, and the capsules were very strong with satisfactory pliability after this storage period.

I claim:

1. A process for the preparation of and gelatin capsules comprising at least partially filling hard gelatin capsule shells with a formulation which is liquid at 25° C. and which comprises (a) a fat-soluble nutrient; (b) a nonionic surfactant; and (c) a gelatin softening agent, wherein said gelatin softening agent is added in an amount sufficient to prevent embrittlement of the hard gelatin capsules.

2. The process of claim 1 further comprising (d) water.

3. The process of claim 1 in which said fat-soluable nutrients comprises a fat-soluable vitamin or a fatty acid glyceride.

4. The process of claim 1 in which said nonionic surfactant comprises a polyoxyethylated compound.

5. The process of claim 4 in which said polyoxyethylated compounds comprise a polyoxyethylated castor oil or a polyoxyethylated hydrogenated castor oil.

6. The process of claim 4 in which said polyoxyethylated compounds comprise a combination of polyoxyethylated castor oil and a polyethylated hydrogenated castor oil.

7. The process of claim 3 in which said nonionic surfactant has an HLB value of at least 10.

8. The process of claim 1, in which said gelatin softening agent comprises glycerol, propylene glycol or glyceryl mono-oleate.

9. The process of claim 8 in which said gelatin softening agent comprises glyceryl mono-oleate.

10. The process for the preparation of a hard gelatin capsule containing a non-gellable fill which is liquid at 25° C., said fill comprising:

(a) a fat-soluble nutrient selected from the group consisting of a fat-soluble vitamin, a fatty acid and a fatty acid glyceride;

(b) a nonionic surfactant; and (c) a gelatin softening agent selected from the group consisting of glycerol, propylene glycol and glyceryl mono-oleate, wherein said gelatin softening agent is added in an amount sufficient to prevent embrittlement of the hard gelatin capsules.

11. The process as claimed in claim 10, further comprising (d) water.

12. The process as claimed in claim 10, wherein said fat-soluble vitamin is selected from the group consisting of vitamin A, vitamin D, vitamin E, and vitamin K.

13. The process as claimed in claim 10, wherein said fatty acid is a $C_{12}$–$C_{24}$ saturated or unsaturated fatty acid.

14. The process as claimed in claim 10, wherein said fatty acid glyceride comprises a mono-, di- or tri-glyceride having at least one $C_{12}$–$C_{24}$ saturated or unsaturated fatty acid chain.

15. The process as claimed in claim 10, wherein said nonionic surfactant has an HLB of at least 10.

16. The process as claimed in claim 10, wherein said nonionic surfactant is a polyoxyethylated compound.

17. The process as claimed in claim 10, wherein said gelatin softening agent comprises glyceryl mono-oleate.

18. The process as claimed in either claim 13 or claim 14, wherein said fatty acid or fatty acid glyceride is present in amounts of 50–300 mg.

19. The process as claimed in claim 10, wherein said nonionic surfactant is present in amounts equal to 30–99% of the total weight; or 50–250 mg.

20. The process as claimed in claim 10, wherein said gel softening agent is present in amounts up to 10% of the total non-oil weight, or 3–6% of the total weight.

21. The process as claimed in claim 17, wherein said glyceryl mono-oleate is present in amounts up to 30% of the total non-oil weight, or 3–25% of the total weight.

22. The process as claimed in claim 12, wherein said vitamin A is present in amounts of 5–150 mg, said vitamin D is present in amounts of 0.001–0.1 mg, said vitamin E is present in amounts of 50–300 mg, and said vitamin K is present in amounts of 0.1–10 mg.

* * * * *